United States Patent
Wolf

(10) Patent No.: US 10,350,026 B2
(45) Date of Patent: Jul. 16, 2019

(54) DENTAL DRILL TOOL

(71) Applicant: James B. Wolf, Pepper Pike, OH (US)

(72) Inventor: James B. Wolf, Pepper Pike, OH (US)

(*) Notice: Subject to any disclaimer, the term of this patent is extended or adjusted under 35 U.S.C. 154(b) by 0 days.

(21) Appl. No.: 15/687,853

(22) Filed: Aug. 28, 2017

(65) Prior Publication Data

US 2018/0055598 A1 Mar. 1, 2018

Related U.S. Application Data

(60) Provisional application No. 62/379,933, filed on Aug. 26, 2016.

(51) Int. Cl.

| | | |
|---|---|---|
| A61C 1/00 | (2006.01) | |
| A61C 1/08 | (2006.01) | |
| A61C 3/02 | (2006.01) | |
| A61C 19/06 | (2006.01) | |
| A61C 1/05 | (2006.01) | |

(52) U.S. Cl.
CPC ............ *A61C 1/081* (2013.01); *A61C 1/0046* (2013.01); *A61C 1/055* (2013.01); *A61C 3/02* (2013.01); *A61C 19/063* (2013.01); *A61C 1/0061* (2013.01)

(58) Field of Classification Search
CPC ....... A61C 3/0025; A61C 1/081; A61C 1/055; A61C 1/0046; A61C 3/02; A61C 19/063; A61C 1/0061; A61C 1/05
See application file for complete search history.

(56) References Cited

U.S. PATENT DOCUMENTS

| | | |
|---|---|---|
| 4,973,247 A | 11/1990 | Varnes |
| 5,326,264 A | 7/1994 | Al Kasem |
| 6,270,342 B1 | 8/2001 | Neuberger |
| 6,441,354 B1 * | 8/2002 | Seghatol .................. A61C 5/00 219/679 |

(Continued)

FOREIGN PATENT DOCUMENTS

GB 847262 A 9/1960

OTHER PUBLICATIONS

Nordenvall, Karl-Johan, In Vivo Resin Impregnation of Dentinal Tubes, Magazine, Dec. 1980, vol. 44 No. 6, Karolinska Institutet School of Dentistry, Stockholm, Sweden.

(Continued)

*Primary Examiner* — Nicholas D Lucchesi
(74) *Attorney, Agent, or Firm* — Eschweiler & Potashnik, LLC

(57) ABSTRACT

A system and method for mitigating pain associated with dentistry provides a removal apparatus for removing a portion of a tooth. A desiccation apparatus flows a desiccated gas to the portion of the tooth to desiccate dentinal tubules in a region surrounding the portion of the tooth, generally preventing nerve cells within the tooth from transmitting pain signals associated with the removal. The removal apparatus has a drill head with a body having an axial opening configured to accept a dental burr. An annular passage exists between the dental burr and the body within the axial opening. A chamber in the body is in fluid communication with the axial opening, where a channel is fluidly coupled to an external port and to a source of the desiccated gas to flow the desiccated gas therethrough and expose a drilling region of the dental burr to the desiccated gas to mitigate pain.

15 Claims, 2 Drawing Sheets

(56) References Cited

U.S. PATENT DOCUMENTS

| | | | |
|---|---|---|---|
| 2005/0233280 A1* | 10/2005 | Hamman | A61C 3/025 |
| | | | 433/88 |
| 2007/0054243 A1 | 3/2007 | Schemmer | |
| 2007/0148619 A1* | 6/2007 | Anderson | A61C 17/043 |
| | | | 433/136 |
| 2010/0167233 A1 | 7/2010 | Dricot | |
| 2012/0039751 A1* | 2/2012 | Shenberg | A61L 2/183 |
| | | | 422/119 |
| 2015/0147718 A1* | 5/2015 | Khakpour | A61C 17/20 |
| | | | 433/81 |

OTHER PUBLICATIONS

International Search Report and Written Opinion dated Nov. 3, 2017 in connection with International Patent Application No. PCT/US2017/048829.

* cited by examiner

DENTAL DRILL TOOL

REFERENCE TO RELATED APPLICATIONS

This application claims the benefit of U.S. Provisional Application No. 62/379,933 filed Aug. 26, 2016, entitled "DENTAL DRILL TOOL", the contents of which are herein incorporated by reference in their entirety.

TECHNICAL FIELD

The present invention relates generally to dental tools, and more specifically to an dental drill and methodology for generally pain-free drilling of a tooth with little to no pharmaceutical anesthesia.

BACKGROUND

Tooth decay or other dental problems often necessitate a drilling of a patient's tooth in order to remove decay or otherwise expose an inner portion of the tooth. Conventionally, pharmaceutical anesthetics, such as local anesthetics including one or more of lidocaine, procaine, or another pharmaceutical anesthetic are injected or otherwise administered to the area surrounding the tooth in order to reduce pain associated with the drilling procedure. In some patients, allergic reactions or other complications can arise due to the administration of the pharmaceutical anesthetic. In other instances, a patient may not desire or may be otherwise averse to a pharmaceutical anesthetics. In such patients, few viable options presently exist to permit both the necessary drilling of the tooth, and the desired reduction in pain associated with said drilling.

SUMMARY

The present disclosure provides a system, apparatus, and method for mitigating pain concurrent with a removal of a portion of a tooth. Accordingly, the following presents a simplified summary of the invention in order to provide a basic understanding of some aspects of the invention. This summary is not an extensive overview of the invention. It is intended to neither identify key or critical elements of the invention nor delineate the scope of the invention. Its purpose is to present some concepts of the invention in a simplified form as a prelude to the more detailed description that is presented later.

In accordance with one exemplary aspect of the present disclosure a system for removing a portion of a tooth is provided, wherein pain associated with the removal of the portion of the tooth is mitigated. The system, according to one example, comprises a removal apparatus configured to remove the portion of the tooth. A desiccation apparatus is further provided and configured to flow a desiccated gas to the portion of the tooth. The desiccated gas, for example, generally desiccates dentinal tubules in a region surrounding the portion of the tooth, therein generally preventing nerve cells within the tooth from transmitting pain signals associated with said removal of the portion of the tooth.

In accordance with one example, the removal apparatus comprises a dental drill having a drill head. The drill head, for example, comprises a body having an axial opening defined therein. The body, for example, is comprised of one or more of a metal, a polymer, and a ceramic, wherein the body is configured to be sterilized via an autoclave. The axial opening, for example, is configured to accept a dental burr therethrough, wherein an annular passage is defined between the dental burr and the body within the axial opening. In one example, the annular passage has a predetermined annular width.

In another example, a chamber is defined within the body, wherein the chamber is in fluid communication with the axial opening. A channel fluidly couples the chamber to an external port, wherein the external port is selectively coupled to a source of the desiccated gas. Accordingly, the channel, chamber, and annular passage of the axial opening are configured to flow the desiccated gas therethrough, thereby generally exposing a drilling region of the dental burr to the desiccated gas.

In one example, the drill head is selectively coupled to a dental drill body, wherein the dental drill body is configured a selectively rotate the dental burr at one or more predetermined speeds. In another example, the dental burr further comprises an axial hole therethrough, wherein the axial hole is further fluidly coupled to the external port. In yet another example, the removal apparatus comprises a laser.

In accordance with another exemplary aspect of the disclosure, a method for mitigating pain in dentistry is provided, such as when removing a portion of a tooth. The method, in accordance with one example, comprises flowing a desiccated gas to a portion of a tooth at a predetermined flow rate. The desiccated gas, for example, comprises one or more of desiccated air and desiccated nitrogen having a low moisture content. Concurrent with flowing the desiccated gas to the portion of the tooth, the portion of the tooth is removed, such as by drilling or laser removal. Accordingly, the desiccated gas generally desiccates dentinal tubules in the tooth, therein generally preventing nerve cells within the tooth from transmitting pain signals associated with said removal of the portion of the tooth.

In one example, removing the portion of the tooth comprises drilling the portion of the tooth via a rotation of a burr of a dental drill, and wherein flowing the desiccated gas to the portion of a tooth comprises flowing the desiccated gas around the burr of the dental drill. Drilling the portion of the tooth, for example, may comprise rotating the burr at one or more predetermined rotational speeds concurrent with the burr contacting the tooth, thereby removing the portion of the tooth via the burr. Accordingly, the desiccated gas generally desiccates dentinal tubules in a region of the tooth contacted by the burr, therein generally preventing the nerve cells associated therewith within the tooth from transmitting pain signals associated with said removal of the portion of the tooth. The one or more predetermined speeds, for example, are respectively associated with one or more layers of the tooth.

In another alternative, removing the portion of the tooth comprises directing a laser at the portion of the tooth concurrent with flowing the desiccated gas thereto. Further, other methods for removing the portion of the tooth are also contemplated.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of a few of the various ways in which the principles of the invention may be employed. Other objects, advantages and novel features of the invention will become apparent from the following detailed description of the invention when considered in conjunction with the drawings.

DETAILED DESCRIPTION

Figure 1:
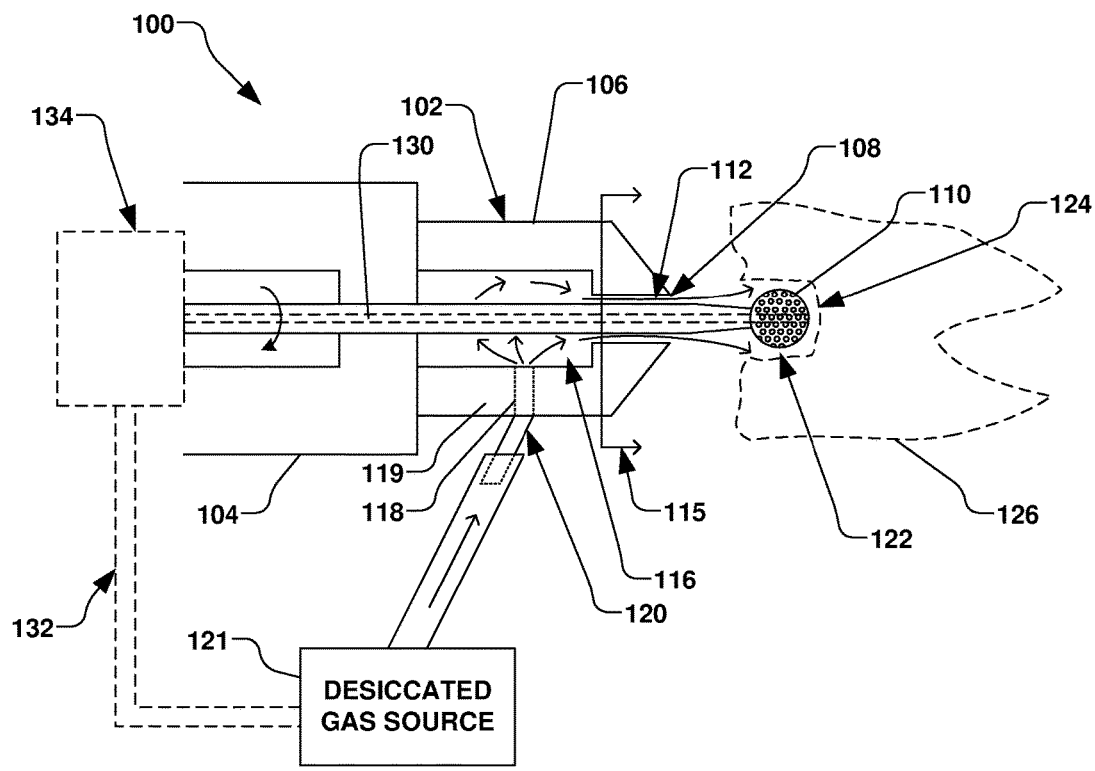
FIG. 1 is a schematic illustrating a dental drilling system in accordance with several examples of the present disclosure.

The present disclosure is directed generally toward systems and methods for providing a generally painless removal of a portion of a tooth without the use conventional pharmaceutical anesthetics. More particularly, the present disclosure is directed toward a method for mitigating pain concurrent with a drilling operation on a tooth and an improved dental drill head configured to desiccate a region of the tooth being removed, whereby the desiccation of the tooth advantageously mitigates pain associated with the drilling of the tooth. The present disclosure discloses a novel approach to mitigating pain, whereby dentinal tubules (also called dental tubules) within the tooth are desiccated concurrent with the drilling operation, thus generally preventing pain receptors within the tooth from transmitting pain to the central nervous system. Not only does the present disclosure provide such a novel approach to mitigating pain, the present disclosure further provides an improvement over conventional dental drill heads and hand pieces used for removing portions of a tooth, whereby the conventional dental drill heads and hand pieces have not been heretofore configured to direct a sufficient supply of dry gas to the cavity within the tooth preparation in order to quickly desiccate the dentinal tubules and provide the presently disclosed pain-free result.

Accordingly, the present invention will now be described with reference to the drawings, wherein like reference numerals may be used to refer to like elements throughout. It is to be understood that the description of these aspects are merely illustrative and that they should not be interpreted in a limiting sense. In the following description, for purposes of explanation, numerous specific details are set forth in order to provide a thorough understanding of the present invention. It will be evident to one skilled in the art, however, that the present invention may be practiced without these specific details. Further, the scope of the invention is not intended to be limited by the embodiments or examples described hereinafter with reference to the accompanying drawings, but is intended to be only limited by the appended claims and equivalents thereof.

It is also noted that the drawings are provided to give an illustration of some aspects of embodiments of the present disclosure and therefore are to be regarded as schematic only. In particular, the elements shown in the drawings are not necessarily to scale with each other, and the placement of various elements in the drawings is chosen to provide a clear understanding of the respective embodiment and is not to be construed as necessarily being a representation of the actual relative locations of the various components in implementations according to an embodiment of the invention. Furthermore, the features of the various embodiments and examples described herein may be combined with each other unless specifically noted otherwise.

It is also to be understood that in the following description, any direct connection or coupling between functional blocks, devices, components, circuit elements or other physical or functional units shown in the drawings or described herein could also be implemented by an indirect connection or coupling. Furthermore, it is to be appreciated that functional blocks or units shown in the drawings may be implemented as separate features or components in one embodiment, and may also or alternatively be fully or partially implemented in a common feature or component in another embodiment.

Dentinal tubules comprise minute, wavy, branching tubes or canals in the dentin of a tooth. The dentinal tubules, for example, contain long cytoplasmic processes of odontoblasts and extend radially from the pulp to the dentoenamel and dentocemental junctions. The present invention presently appreciates that dentinal tubules within a tooth, when desiccated sufficiently, can prevent the transmission of pain to the nervous system of the patient.

When removing one or more portions of a tooth, conventional dental drills have been used for many years. Such conventional dental drills utilize liquid(s), such as water, to cool the tooth during drilling, whereby the liquid(s) are applied to the tooth and cavity drilled, therein. However, the present invention presently appreciates that the use of such liquid(s) during drilling can generally promote the transmission of pain via the dentinal tubules within the tooth. The present disclosure thus seeks to prevent the transmission or conduction of pain via the interaction of the liquid(s) and dentinal tubules by generally eliminating the liquid(s) concurrent with the drilling operation and replacing the liquid(s) with a supply of desiccated gas to the drilling site.

Accordingly, the present invention advantageously utilizes desiccated gas (e.g., a gas having a low moisture content) to not only cool the tooth concurrent with drilling, but also utilizes the desiccated gas to substantially dry or desiccate the dentinal tubules within the tooth, thereby generally preventing the transmission of pain and advantageously mitigating or eliminating the use of other problematic pharmaceutical anesthetics used in conventional procedures. It should be noted that the desiccated gas described in the present disclosure may comprise any gas or combination of gases (e.g., air, nitrogen, etc.) having a substantially low moisture content sufficient to prevent or substantially limit the transmission of pain through the dentinal tubules. While the desiccated gas may have zero moisture content in some examples, some small amount of moisture may likewise be present in the desiccated gas, while still falling within the scope of the present disclosure and providing the desired limitation of pain transmission through the dentinal tubules.

In accordance with one example of the present disclosure, FIG. 1 illustrates an exemplary dental drilling system 100. The dental drilling system 100 of FIG. 1, for example, comprises a drill head 102 operably coupled to a dental drill body 104 (also called a hand-piece). The drill head 102, for example, comprises a gas flow element 106 (e.g., a vessel, air collector, concentrator, or the like) operably coupled to the drill head, wherein the gas flow element has an axial opening 108 defined therein. The axial opening 108 in the gas flow element 106, for example, is configured to accept a dental burr 110 therethrough. The dental burr 110 (also called a drill bit), for example, is operably coupled to the dental drill body 104, wherein the dental drill body comprises a motor (not shown) configured to selectively rotate the dental burr at one or more predetermined speeds.

Figure 2:
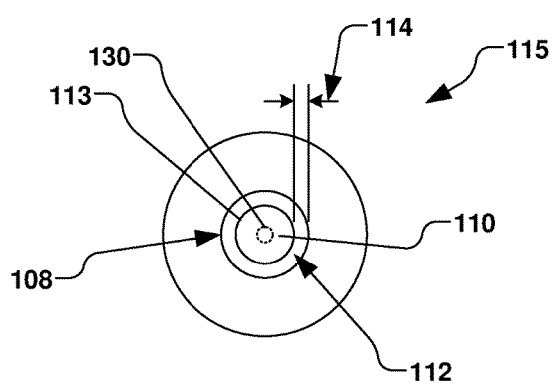
FIG. 2 is a cross-sectional view of a drill head in accordance with several examples of the present disclosure.

An annular passage 112 is generally defined between a shaft 113 of the dental burr 110 and the gas flow element 106 within the axial opening 108 wherein the annular passage has a predetermined annular width 114, as shown in cross-section 115 in FIG. 2. Dimensions of the annular passage 112, such as the predetermined annular width 114, for example, may be calculated to provide a substantially laminar flow therethrough at one or more predetermined pressures. The gas flow element 106 of FIG. 1, for example, is configured to be selectively coupled to the dental drill body 104, such as by one or more screw threads, cam lever apparatus, friction-fit, or the like, wherein the gas flow element may be selectively removed from the drill body for sterilization. The gas flow element 106, for example, may be comprised of one or more of a metal (e.g., stainless steel), polymer, ceramic, or other autoclaveable material.

A chamber 116, for example, is further defined within the gas flow element 106, wherein the chamber is in fluid communication with the axial opening 108. In one example, a channel 118 extends radially through a wall 119 of the gas flow element 106, wherein the channel provides a fluid communication between the chamber 116 and an external port 120. The external port 120, for example, is configured to be selectively coupled to a desiccated gas source 121, wherein the external port thus provides a fluid communication between the chamber 116 and the desiccated gas source. As such, the desiccated gas source 121 is configured to flow a desiccated gas (e.g., desiccated air, desiccated nitrogen, or other desiccated gas or substantially dry gas(es)) through the channel 118, chamber 116, and annular passage 112 to the axial opening 108, thereby generally exposing a drilling region 122 of the dental burr 110 to the desiccated gas.

In the present example, the annular passage 112 thus provides the desiccated gas from the desiccated gas source 121 to the drilling region 122 by flowing the desiccated gas generally around the dental burr 110 (referred to as "Around The Burr"-ATB). The drilling region 122 of the dental burr 110, for example, may be associated with a cavity 124 of a tooth 126 that is to undergo drilling, cavity filling, or other dental procedure(s). The dental burr 110, for example, may be fitted to the dental drill body 104 that is configured to rotate the dental burr at any speed.

It should be noted that the size and configuration of the chamber 116, annular passage 112, axial opening 108, and other portions of the drill head 102 may be determined based on various factors, such as the pressure of the desiccated gas flowed therethrough, the size (e.g., length, diameter) of the dental burr 110, the desired depth of drilling, and other factors, and that the sizes and configurations shown and described herein are not to be considered as limiting, but as examples of some embodiments of the present disclosure.

In accordance with another example, as opposed to flowing the desiccated gas through the annular passage 112 as described above, the dental burr 110 may comprise an axial hole 130 therethrough. An optional external port 132 may be coupled to the drill body 104 via a port member 134 to fluidly couple the axial hole 130 of the dental burr 110 to the desiccated gas source 120. The port member 134 may be formed from various materials, such as plastic, resin, metal, etc. In one example, the axial hole 130 is further fluidly coupled to the external port 118. For example, the axial hole 130 may be fluidly coupled to the external port 118 via the chamber 116, whereby the desiccated gas may further flow through the axial hole (e.g., Through The Burr—TTB) to optionally or additionally desiccate the tooth 126 concurrent with removal of portions of the tooth via the rotation of the dental burr 110. While not shown, the axial hole 130 may further comprise a plurality of holes or passages through the dental burr 110, whereby the plurality of holes may be offset to provide additional flow of the desiccated gas to the tooth 126.

In accordance with the present disclosure, the exemplary dental drilling system 100 is configured to direct sufficient pressure and flow of the desiccated gas to the cavity 124 within the tooth 126 to quickly desiccate the dentinal tubules associated with the tooth, thus mitigating pain concurrent with removal of decay associated with the cavity.

In accordance with another aspect of the present invention, FIG. 2 illustrates an exemplary method 200 for desiccating a tooth concurrent with a removal of a portion of the tooth, whereby the desiccation mitigates pain associated with said removal. It should be noted that while exemplary methods are illustrated and described herein as a series of acts or events, it will be appreciated that the present invention is not limited by the illustrated ordering of such acts or events, as some steps may occur in different orders and/or concurrently with other steps apart from that shown and described herein, in accordance with the invention. In addition, not all illustrated steps may be required to implement a methodology in accordance with the present invention. Moreover, it will be appreciated that the methods may be implemented in association with the systems illustrated and described herein as well as in association with other systems not illustrated.

Figure 3:
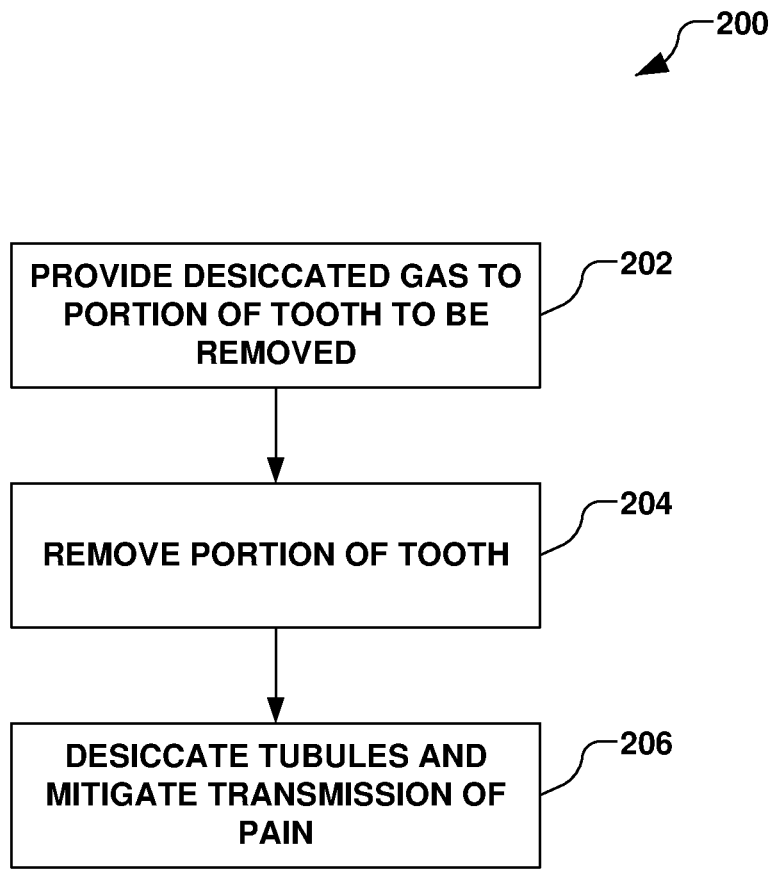
FIG. 3 is an example methodology for minimizing pain concurrent with a removal of a portion of a tooth.

As illustrated in FIG. 3, the method 200 begins with providing a desiccated gas to a region of a tooth in act 202. The region of the tooth, for example comprises a cavity or other portion of a tooth that is to be removed or repaired. In one example, the desiccated gas is provided in act 202 via a dental drill, such as described in the dental drilling system 100 of FIG. 1.

In act 204 of FIG. 3, a portion of the tooth is removed. For example, the tooth may be drilled by a dental burr 110 associated with the dental drilling system 100 of FIG. 1, whereby the dental burr is rotated at one or more predetermined rotational speeds, based, for example, on the region of the tooth being drilled. For example, an outer region of the tooth may be associated with a first rotational speed, and an interior region of the tooth may be associated with a second rotational speed. For example, a low rotational speed may be utilized to mitigate heat build-up associated with abrasion and friction between the dental burr 110 and the tooth 126, while a higher rotational speed may be utilized to reduce vibration and provide a faster treatment time. In act 206, dentinal tubules associated with the tooth are desiccated via the desiccated gas supplied in act 202. For example, the desiccated gas is supplied to the region at which the dental burr 110 contacts the tooth 126 shown in FIG. 1. In accordance with the present disclosure, the desiccated gas (e.g., desiccated air) substantially dries the tubules, therein substantially blocking pain receptors within the tooth from sensing and/or transmitting pain signals to the nervous system of the person undergoing the procedure.

Furthermore, the disclosure presently appreciates that the desiccation of the dentinal tubules provided by the apparatus and method disclosed herein can further provide sufficient time to perform additional operations on the tooth 126. For example, once the dentinal tubules are desiccated, several minutes may transpire before the dentinal tubules regain fluid from the body, whereby this time may be advantageously utilized to place an acidic etch compound on the tooth. The acidic etch compound prepares the tooth 126 for subsequent filling, whereby the desiccation of the dentinal tubules described above advantageously mitigates irritation that has been previously seen in conventional dentistry when placing such an acidic etch compound on the tooth.

It should be noted that while the present disclosure discusses a drilling of a tooth, the present invention contemplates the use of any apparatus configured for removing a portion of a tooth, whereby the presently disclosed method for desiccating the dentinal tubules of the tooth concurrent with the removal operation advantageously mitigates pain associated with the procedure. It should be further noted that the present invention may be practiced by providing desiccated gas to the tooth using various other systems or apparatuses configured to direct a flow of gas, and that the removal of the portion of the tooth may be accomplished using various dental systems or apparatuses such as lasers or various other removal apparatuses.

Although the invention has been shown and described with respect to a certain embodiment or embodiments, it should be noted that the above-described embodiments serve only as examples for implementations of some embodiments of the present invention, and the application of the present invention is not restricted to these embodiments. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application. Accordingly, the present invention is not to be limited to the above-described embodiments, but is intended to be limited only by the appended claims and equivalents thereof.

The invention claimed is:

1. A drill head for a dental drill, the drill head comprising:
a body having an axial opening defined therein, wherein the axial opening is configured to accept a dental burr therethrough, and wherein an annular passage is defined between the dental burr and the body within the axial opening, and wherein the annular passage has a predetermined annular width;
a chamber defined within the body, wherein the chamber is in fluid communication with the axial opening; and
a channel fluidly coupling the chamber to an external port, wherein the external port is configured to be selectively coupled to a source of desiccated gas, whereby the channel, chamber, and annular passage of the axial opening are configured to flow the desiccated gas therethrough, thereby generally exposing a drilling region of the dental burr to the desiccated gas.

2. The drill head of claim 1, wherein the body is comprised of one or more of a metal, a polymer, and a ceramic.

3. The drill head of claim 2, wherein the drill head is configured to be selectively coupled to a dental drill body, wherein the dental drill body is configured to selectively rotate the dental burr at one or more predetermined speeds.

4. The drill head of claim 1, wherein the dental burr further comprises an axial hole therethrough, wherein the axial hole is further fluidly coupled to the external port.

5. A method for mitigating pain associated with a tooth in dentistry, the method comprising:
flowing a desiccated gas to a portion of the tooth at a predetermined flow rate;
removing the portion of the tooth concurrent with flowing the desiccated gas thereto, wherein the desiccated gas generally desiccates dentinal tubules in the tooth, therein generally preventing nerve cells within the tooth from transmitting pain signals associated with said removal of the portion of the tooth.

6. The method of claim 5, wherein removing the portion of the tooth comprises drilling the portion of the tooth via a rotation of a burr of a dental drill, and wherein flowing the desiccated gas to the portion of a tooth comprises flowing the desiccated gas around the burr of the dental drill.

7. The method of claim 6, wherein drilling the portion of the tooth comprises rotating the burr at one or more predetermined rotational speeds concurrent with the burr contacting the tooth, thereby removing the portion of the tooth via the burr, and wherein the desiccated gas generally desiccates dentinal tubules in a region of the tooth contacted by the burr, therein generally preventing nerve cells within the tooth from transmitting pain signals associated with said removal of the portion of the tooth.

8. The method of claim 7, wherein the one or more predetermined speeds are respectively associated with one or more layers of the tooth.

9. The method of claim 5, wherein the desiccated gas comprises one or more of desiccated air and desiccated nitrogen.

10. The method of claim 5, wherein removing the portion of the tooth comprises directing a laser at the portion of the tooth concurrent with flowing the desiccated gas thereto.

11. A system for mitigating pain associated with a tooth concurrent with a removal of a portion of the tooth, the system comprising:
a removal apparatus configured to remove the portion of the tooth; and
a desiccation apparatus configured to flow a desiccated gas to the portion of the tooth concurrent with the removal apparatus removing the portion of the tooth, wherein the desiccated gas generally desiccates dentinal tubules in a region surrounding the portion of the tooth, therein generally preventing nerve cells within the tooth from transmitting pain signals associated with said removal of the portion of the tooth.

12. The system of claim 11, wherein the removal apparatus comprises a laser.

13. A system for mitigating pain associated with a tooth concurrent with a removal of a portion of the tooth, the system comprising:
a removal apparatus configured to remove the portion of the tooth; and
a desiccation apparatus configured to flow a desiccated gas to the portion of the tooth, wherein the desiccated gas generally desiccates dentinal tubules in a region surrounding the portion of the tooth, therein generally preventing nerve cells within the tooth from transmitting pain signals associated with said removal of the portion of the tooth, wherein the removal apparatus comprises:
a dental drill having a drill head, the drill head comprising:
a body having an axial opening defined therein, wherein the axial opening is configured to accept a dental burr therethrough, and wherein an annular passage is defined between the dental burr and the body within the axial opening, and wherein the annular passage has a predetermined annular width;
a chamber defined within the body, wherein the chamber is in fluid communication with the axial opening; and
a channel fluidly coupling the chamber to an external port, wherein the external port is selectively coupled to a source of the desiccated gas, whereby the channel, chamber, and annular passage of the axial opening are configured to flow the desiccated gas therethrough, thereby generally exposing a drilling region of the dental burr to the desiccated gas.

14. The system of claim 13, wherein the drill head is selectively coupled to a dental drill body, wherein the dental drill body is configured to selectively rotate the dental burr at one or more predetermined speeds.

15. The system of claim 13, wherein the dental burr further comprises an axial hole therethrough, wherein the axial hole is further fluidly coupled to the external port.

* * * * *